(12) United States Patent
Sonntag et al.

(10) Patent No.: US 6,830,843 B2
(45) Date of Patent: Dec. 14, 2004

(54) METHOD FOR CONTROLLING THE QUALITY OF THE COOLANT FOR FUEL CELL SYSTEMS

(75) Inventors: Anton Sonntag, Kirchheim (DE); Josef Sonntag, Kirchheim (DE); Hubert Urban, Ohmden (DE)

(73) Assignee: Ballard Power Systems AG, Kirchheim-Nabern (DE)

(*) Notice: Subject to any disclaimer, the term of this patent is extended or adjusted under 35 U.S.C. 154(b) by 64 days.

(21) Appl. No.: 10/051,389

(22) Filed: Jan. 22, 2002

(65) Prior Publication Data
US 2002/0106543 A1 Aug. 8, 2002

(30) Foreign Application Priority Data
Jan. 19, 2000 (DE) .......................................... 101 02 247

(51) Int. Cl.[7] .............................................. H01M 8/04
(52) U.S. Cl. .............................. 429/24; 429/22; 429/23
(58) Field of Search ............................... 429/22, 23, 24

(56) References Cited

U.S. PATENT DOCUMENTS 5,760,488 A   6/1998  Sonntag
6,582,840 B2 * 6/2003  Hortop ......................... 429/13

FOREIGN PATENT DOCUMENTS

DE        19503749      4/1996
EP         0043941      1/1982

* cited by examiner

Primary Examiner—Dah-Wei Yuan
(74) Attorney, Agent, or Firm—Seed IP Law Group PLLC

(57) ABSTRACT

A method for controlling the quality of the coolant for fuel cell systems, it being proposed to measure and monitor the insulation resistance of the load circuit of the fuel cell system. It has become apparent that there is a functional, uniquely defined relationship between the measured insulation resistance and the electrical conductivity of the coolant so that a separate measurement of the electrical conductivity by means of corresponding sensor systems and evaluation means can be dispensed with in the present invention.

4 Claims, 1 Drawing Sheet

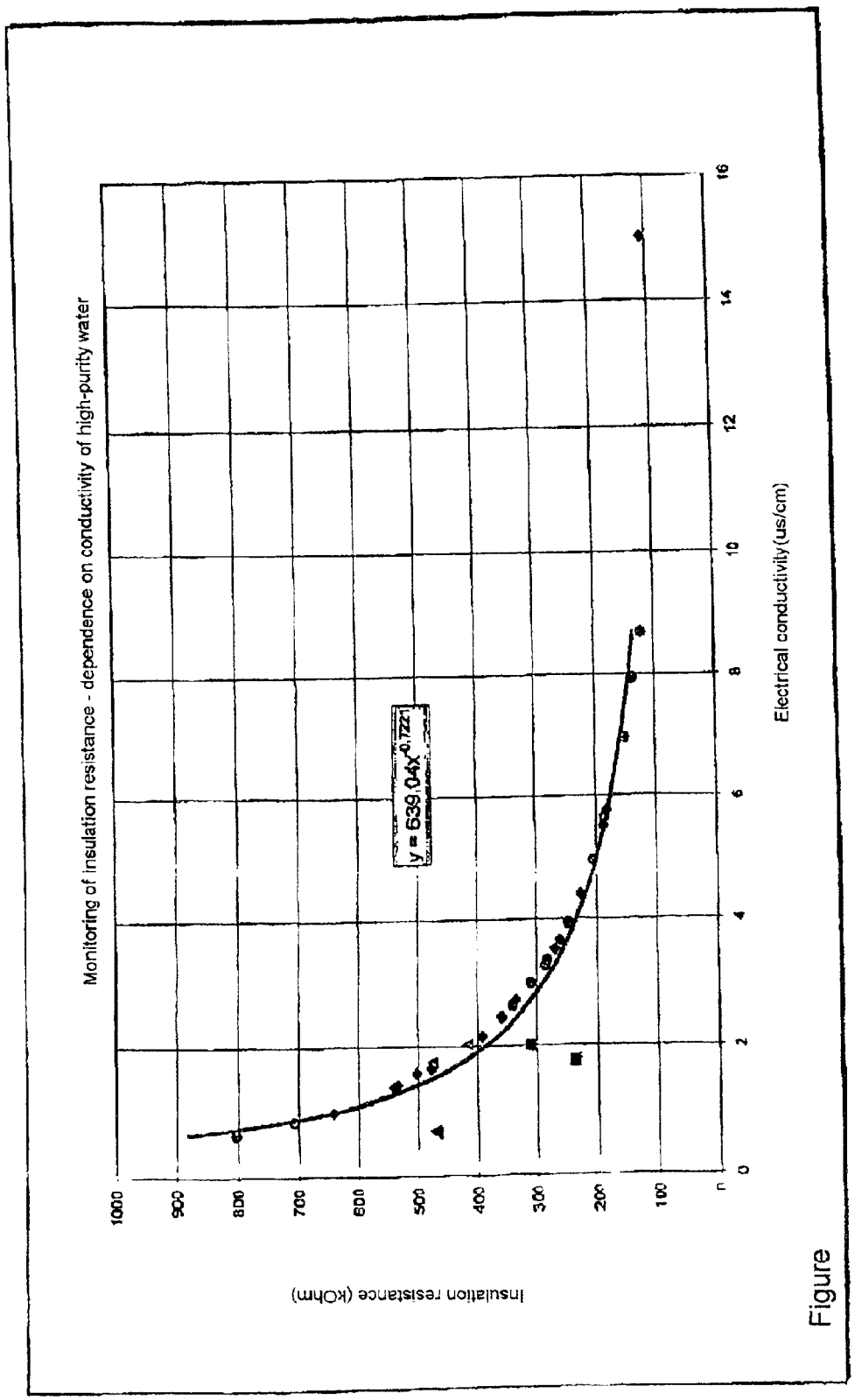
Figure

METHOD FOR CONTROLLING THE QUALITY OF THE COOLANT FOR FUEL CELL SYSTEMS

BACKGROUND AND SUMMARY OF THE INVENTION

This application claims the priority of German Patent DE 101 02 247.6, filed Jan. 19, 2001, the disclosure of which is expressly incorporated by reference herein.

The invention relates to a method for controlling the quality of the coolant, such as cooling water, for fuel cell systems.

Such a method is known from EP 0 043 941 B1. In said application, the foreign ion content of water is continuously monitored using a conductivity measurement, the water being cooled to a temperature between 0 and 5° C. before the measurement. It has been found that there is a greatly increased relative conductivity (related to high-purity water) in this temperature range in comparison with a measurement at ambient temperature or at higher temperatures.

This known quality control is also applied in fuel cell systems in which the foreign ion concentration in the cooling water should not exceed a specific value. For this purpose, a conductivity sensor measures the electrical conductivity of the cooling water. The use of such a conductivity sensor is, however, associated with additional effort and costs. At the temperatures which occur, there is also a poor signal-to-noise ratio. Such prior cooling of the cooling water for measuring the conductivity, as proposed in EP 0 043 941 B1, would further increase the costs and the effort.

The object of the present invention is therefore to specify a quality control for coolants such as cooling water for fuel cell systems, which operates without additional effort and costs, but with a high degree of reliability.

This object is achieved according to the invention by means of a method for controlling coolant quality of a fuel cell system via measuring the insulation resistance of the load circuit. In a preferred embodiment, the method comprises establishing a relationship between the electrical conductivity of the coolant and the insulation resistance of the load circuit; measuring the insulation resistance of the load circuit to determine the electrical conductivity; and monitoring the electrical conductivity of the coolant. Further advantageous refinements will be evident from the following description.

According to the invention, the insulation resistance of the load circuit of the fuel cell system is measured and monitored. It has specifically been found that the insulation resistance has a relationship with the quality of the fuel cell coolant (cooling water) and thus with the electrical conductivity of this coolant. Because, for safety reasons, the insulation of the load current lines in fuel cell systems is generally monitored, conclusions about the coolant (cooling water) quality of the fuel cell system can be drawn by means of the invention from the monitoring of the insulation resistance without additional effort.

A suitable method for monitoring the insulation resistance of a load circuit of a fuel cell system is disclosed in DE-195 03 749 C1, corresponding to U.S. Pat. No. 5,760,488, which is incorporated herein by reference in its entirety. In said publication, it is proposed to implement the fuel cell-fed or battery-fed power supply system of a vehicle as an IT system (See Association of German Electrotechnical Engineers, Draft Standard Concerning DIN VDE 0100, Part 410, A3, Section 413, June, 1989) in which the loads which are connected to the load circuit are electrically connected to the bodywork of the vehicle with low impedance. The load circuit lines are preferably placed symmetrically at a potential above or below the potential of the bodywork of the vehicle here and connected to the bodywork of the vehicle at high impedance. Damage (for example damage to the fuel cell stack or short-circuiting of the load circuit line to the vehicle bodywork) can be detected by means of a measuring bridge balancing stage and a measuring signal-conditioning isolating amplifier stage. The way of implementing an insulation resistance monitoring system is described in detail in the aforesaid document DE 195 03 749 C1. The following is restricted to the details which are relevant to the present invention so that for further details on the insulation resistance monitoring means, the aforesaid document is referred to expressly.

In an advantageous refinement of the invention, a lower threshold value of the insulation resistance of the load circuit of the fuel cell system is defined, and when the insulation resistance drops below this value, the replacement of the coolant which is due is indicated. This indication is given by means of a visual signal, an audible signal or a combined signal.

In a further refinement, a further threshold value of the insulation resistance which is preferably below the first-mentioned value is defined, and when the insulation resistance drops below this threshold value the entire fuel cell system is shut down. In this case, the quality of the coolant has degenerated drastically to the extent that the coolant (cooling water) is no longer suitable for further use in the fuel cell system. The associated threshold value of the insulation resistance can be greater than or equal to that threshold value at which damage has occurred as a result of short-circuiting, leakage currents or damage to the fuel cell stack.

By making different selections of the threshold values of the insulation resistance for the quality control of the coolant, on the one hand, and for the insulation control of the load current lines, on the other, it is possible to distinguish the type of fault or damage which occurs, i.e. different indications can be given for decreasing quality of the cooling water and for poor or missing insulation of the lines.

Furthermore, the insulation resistance and the electrical conductivity of the coolant (cooling water) in the fuel cell system can be measured as a function of one another and the associated value of the electrical conductivity can be assigned to each measured value of the insulation resistance by reference to the relationship which is determined. In fact, it has become apparent that in a predefined system there is a fixed relationship between the electrical conductivity of the cooling water and the insulation resistance of the fuel cell system, this relationship behaving approximately as a 1/x function.

For individual fuel cell systems, or for a class of fuel cell systems, it is thus possible to determine a relationship between the insulation resistance and the electrical conductivity and to define a corresponding function. The upward transgression of the electrical conductivity above specific threshold values then corresponds to the downward transgression of the insulation resistance below correspondingly different threshold values. This transformation can consequently be carried out in a simple way so that previous methods for quality control of the cooling water, which operate by measuring the electrical conductivity, can quickly be transformed to the method according to the invention.

An exemplary embodiment will explain the invention and its advantages in more detail with reference to the appended FIGURE.

The single FIGURE shows the functional relationship between the insulation resistance and the electrical conductivity in a fuel cell system.

In a fuel cell system for driving a motor vehicle, it is possible, as the invention has shown, to determine the insulation resistance of the load circuit of the fuel cell system as a function of the electrical conductivity of the cooling water and to put it graphically in the form of the appended FIGURE. A person skilled in the art is sufficiently familiar with the measurement of the electrical conductivity of the cooling fluid by means of a conductivity sensor. The measurement of the insulation resistance is described in detail, as already mentioned, in DE 195 03 749 C1. In order to avoid repetitions, reference will be made expressly at this point to the content of this document.

It has become apparent that for various fuel cell systems of the same type, a functional relationship between the insulation resistance and the electrical conductivity can be derived, which relationship can be represented by the following function $$y = 639.04\, X^{-0.7221}$$

given the dimensional relationships specified in the FIGURE.

The insulation resistance is given in the FIGURE in kOhm, and the electrical conductivity in $\mu S/cm$. This functional relationship represents, as is apparent from the FIGURE, a good approximation to the actual conditions (measuring points). A uniquely defined assignment of the electrical conductivity to corresponding values of the insulation resistance is thus possible. Consequently, known, upper threshold values for electrical conductivity, above which cooling water is to be replaced or the system is even to be shut down, can be transformed into corresponding, lower threshold values for the insulation resistance. If the insulation resistance of the fuel cell system is monitored, which is generally the case for safety reasons, the measurement results can be re-used directly for the quality control of the coolant which is used, with the result that a separate sensor system with evaluation means connected downstream can be dispensed with.

The invention can be implemented particularly advantageously and cost-effectively in the fuel cell drives for vehicles and integrated into existing systems.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed:

1. A method for determining coolant quality of a fuel cell system which comprises a load circuit having an insulation resistance, the method comprising:

determining the insulation resistance of the load circuit; and determining said coolant quality as a function of determined insulation resistance values.

2. The method of claim 1, further comprising defining a first threshold value for the insulation resistance and signaling a need for the replacement of coolant when the insulation resistance is below the first threshold value.

3. The method of claim 2, wherein the signaling is via at least one of a visual means and an audio means.

4. The method of claim 1, further comprising defining a second threshold value for the insulation resistance and shutting down the fuel cell system when the insulation resistance is below the second threshold value.

* * * * *

UNITED STATES PATENT AND TRADEMARK OFFICE
CERTIFICATE OF CORRECTION

PATENT NO. : 6,830,843 B2
DATED : December 14, 2004
INVENTOR(S) : Anton Sonntag et al.

It is certified that error appears in the above-identified patent and that said Letters Patent is hereby corrected as shown below:

Title page,
Item [30], Foreign Application Priority Data, "Jan. 19, 2000 (DE)" should read as -- Jan. 19, 2001 (DE) --.

Signed and Sealed this

Sixteenth Day of August, 2005

JON W. DUDAS
*Director of the United States Patent and Trademark Office*